(12) United States Patent
Wormser et al.

(10) Patent No.: US 12,318,074 B2
(45) Date of Patent: Jun. 3, 2025

(54) DISPOSABLE URINE COLLECTION CONTAINER

(71) Applicant: Honorix Ltd., Kiryat Shmona (IL)

(72) Inventors: Hava Geula Wormser, Kiryat Shmona (IL); Reuven Marko, Netanya (IL); Haim Danino, Petach Tikva (IL); Chizkiyahu Baer, Dolev (IL)

(73) Assignee: Honorix Ltd., Kiryat Shmona (IL)

( * ) Notice: Subject to any disclaimer, the term of this patent is extended or adjusted under 35 U.S.C. 154(b) by 408 days.

(21) Appl. No.: 17/804,182

(22) Filed: May 26, 2022

(65) Prior Publication Data

US 2022/0287691 A1    Sep. 15, 2022

Related U.S. Application Data

(63) Continuation of application No. PCT/US2020/062314, filed on Nov. 25, 2020.

(60) Provisional application No. 62/941,282, filed on Nov. 27, 2019.

(51) Int. Cl.
*A61B 10/00* (2006.01)
*A61F 5/44* (2006.01)
*A61F 5/443* (2006.01)
*A61M 39/10* (2006.01)
*A61M 39/16* (2006.01)

(52) U.S. Cl.
CPC .......... *A61B 10/007* (2013.01); *A61F 5/4405* (2013.01); *A61F 5/443* (2013.01); *A61M 39/105* (2013.01); *A61M 39/162* (2013.01)

(58) Field of Classification Search
CPC ...... A61B 10/007; A61F 5/4405; A61F 5/443; A61F 5/04; A61F 5/453; A61F 5/4404; A61F 5/445; A61F 13/15; A61F 5/4401; A61F 2013/15146; A61M 39/105; A61M 39/162; A61M 25/0017; A61M 1/80
See application file for complete search history.

(56) References Cited

U.S. PATENT DOCUMENTS

| | | | |
|---|---|---|---|
| 3,340,876 A | 9/1967 | Hill | |
| 3,583,388 A | 6/1971 | Hovick | |
| 3,680,543 A | 8/1972 | Cox | |
| 3,722,503 A | 3/1973 | Hovick | |

(Continued)

FOREIGN PATENT DOCUMENTS

| | | |
|---|---|---|
| CN | 203719957 U | 7/2014 |
| EP | 2068717 B1 | 3/2013 |

(Continued)

OTHER PUBLICATIONS

Search and Examination report for GB2207866.1, dated Sep. 19, 2023, UK Intellectual Property Office, Newport, South Wales, United Kingdom.

(Continued)

*Primary Examiner* — Kai H Weng
*Assistant Examiner* — Alessandro R Del Priore
(74) *Attorney, Agent, or Firm* — M&B IP Analysts, LLC

(57) ABSTRACT

A urine sampling container is provided. The container includes a container shell made of a non-porous material, wherein the container shell includes an orifice through which urine enters into the container shell; and a layer of a water-absorbent resin deposited over at least a bottom portion internal to the container shell.

7 Claims, 3 Drawing Sheets

(56) References Cited

U.S. PATENT DOCUMENTS

| | | | |
|---|---|---|---|
| 3,894,845 A | 7/1975 | Mcdonald | |
| 3,943,770 A | 3/1976 | McDonald | |
| 3,988,209 A | 10/1976 | McDonald | |
| 4,046,138 A | 9/1977 | Libman et al. | |
| 4,064,760 A | 12/1977 | Benjamin | |
| 4,084,589 A | 4/1978 | Kulvi | |
| 4,176,412 A | 12/1979 | Peterson | |
| 4,198,979 A | 4/1980 | Cooney et al. | |
| 4,203,169 A | 5/1980 | Dale | |
| 4,246,901 A | 1/1981 | Frosch et al. | |
| 4,252,132 A | 2/1981 | Kuntz | |
| 4,276,889 A | 7/1981 | Kuntz et al. | |
| 4,331,162 A | 5/1982 | Kuntz et al. | |
| 4,393,881 A | 7/1983 | Shah | |
| 4,420,539 A | 12/1983 | Kostikov et al. | |
| 4,492,258 A | 1/1985 | Lichtenstein et al. | |
| 4,494,581 A | 1/1985 | Gordon | |
| 4,533,354 A * | 8/1985 | Jensen | A61F 5/44 383/44 |
| 4,557,274 A | 12/1985 | Cawood | |
| 4,569,090 A | 2/1986 | Muller | |
| 4,753,249 A | 6/1988 | Muller | |
| 5,067,821 A * | 11/1991 | Young | A61F 5/44 383/44 |
| 5,300,052 A | 4/1994 | Kubo | |
| 5,368,583 A * | 11/1994 | Fleury | A61B 10/007 600/580 |
| 5,380,289 A * | 1/1995 | Hemstreet | A61B 10/007 600/584 |
| 5,409,473 A | 4/1995 | Rosenshein | |
| 5,484,572 A | 1/1996 | Katakura et al. | |
| 5,518,003 A | 5/1996 | Allan | |
| 5,711,310 A | 1/1998 | Vinayagamoorthy et al. | |
| 5,766,136 A | 6/1998 | Cawood | |
| 6,068,618 A | 5/2000 | Anderson | |
| 6,887,223 B2 | 5/2005 | Bisbee | |
| 6,922,852 B1 | 8/2005 | Blum | |
| 7,172,559 B2 | 2/2007 | Yong et al. | |
| 7,195,602 B2 | 3/2007 | Yong et al. | |
| 7,585,293 B2 | 9/2009 | Vermaak | |
| 8,075,538 B2 | 12/2011 | Vernon | |
| 8,079,562 B1 | 12/2011 | Denman | |
| 8,297,577 B1 | 10/2012 | Denman | |
| 8,388,585 B2 | 3/2013 | Tomes et al. | |
| 8,388,587 B1 | 3/2013 | Gmuer et al. | |
| 8,597,207 B1 | 12/2013 | Perry | |
| 8,608,718 B1 | 12/2013 | Patterson-Young | |
| 8,672,909 B2 | 3/2014 | Mukuta | |
| 9,308,118 B1 | 4/2016 | Dupree et al. | |
| 9,456,937 B2 | 10/2016 | Ellis | |
| 9,693,889 B2 | 7/2017 | Schertiger | |
| 9,713,548 B2 | 7/2017 | Amerson | |
| 9,737,433 B2 | 8/2017 | Joh | |
| 9,867,731 B2 | 1/2018 | Mitts | |
| 9,931,012 B2 | 4/2018 | Ichikawa et al. | |
| 9,931,102 B1 * | 4/2018 | Studer | A61B 10/007 |
| 9,974,520 B2 | 5/2018 | Kramer et al. | |
| 10,076,635 B2 | 9/2018 | Macy et al. | |
| 10,376,406 B2 | 8/2019 | Newton | |
| 11,045,246 B1 | 6/2021 | Schwartz | |
| 11,197,659 B2 | 12/2021 | Forte | |
| 2004/0025798 A1 | 2/2004 | Lee et al. | |
| 2005/0004538 A1 | 1/2005 | Forte | |
| 2006/0064033 A1 | 3/2006 | Stewart et al. | |
| 2006/0064034 A1 | 3/2006 | Stewart et al. | |
| 2006/0149164 A1 | 7/2006 | Lee et al. | |
| 2007/0031999 A1 | 2/2007 | Ho et al. | |
| 2007/0185466 A1 | 8/2007 | Co | |
| 2011/0040272 A1 | 2/2011 | Forte et al. | |
| 2011/0107824 A1 | 5/2011 | Lv | |
| 2011/0237977 A1 | 9/2011 | Knight et al. | |
| 2012/0029452 A1 | 2/2012 | Rødsten | |
| 2012/0210503 A1 | 8/2012 | Anzivino et al. | |
| 2013/0237964 A1 | 9/2013 | Kicos | |
| 2013/0269095 A1 | 10/2013 | Finley | |
| 2014/0303516 A1 | 10/2014 | Schneider | |
| 2016/0022249 A1 | 1/2016 | Forte | |
| 2016/0113811 A1 * | 4/2016 | Dupree | A61F 5/441 604/351 |
| 2017/0020645 A1 | 1/2017 | Behan | |
| 2019/0159927 A1 | 5/2019 | Alhaqqan | |
| 2022/0079567 A1 | 3/2022 | Forte | |

FOREIGN PATENT DOCUMENTS

| | | |
|---|---|---|
| JP | 2014195430 A | 10/2014 |
| WO | 2006063979 A1 | 6/2006 |
| WO | 2014135856 A1 | 9/2014 |
| WO | WO-2018056953 A1 * | 3/2018 |

OTHER PUBLICATIONS

International Search Report and Written Opinion of International Searching Authority for PCT/US2020/062314, ISA/RU, Moscow, Russia, Dated: Feb. 4, 2021.

Search and Examination Report for GB2207866.1, dated Nov. 24, 2023, UK Intellectual Property Office, Newport, South Wales, United Kingdom.

Search and Examination Report for GB2207866.1, dated Apr. 3, 2024, UK Intellectual Property Office, Newport, South Wales, United Kingdom.

Search and Examination Report for GB2207866.1,UK Intellectual Property Office, dated Jan. 19, 2024, Newport, South Wales, United Kingdom.

Search and Examination report for GB2207866.1, dated Jul. 4, 2023, UK Intellectual Property Office, Newport, South Wales, United Kingdom.

* cited by examiner

DISPOSABLE URINE COLLECTION CONTAINER

CROSS-REFERENCE TO RELATED APPLICATIONS

This application is a continuation of International Application No. PCT/US2020/062314, filed on Nov. 25, 2020, now pending, which claims the benefit of U.S. Provisional Application No. 62/941,282 filed on Nov. 27, 2019. The contents of the above-referenced applications are hereby incorporated by reference.

TECHNICAL FIELD

The disclosure generally relates to a device for collecting a sample of midstream urine from a patient.

BACKGROUND

For the purpose of diagnosis of patients for testing and analysis, it is frequently necessary to collect a urine sample provided by the patient. In a typical application, the urine sample is analyzed to determine concentrations of chemical substances, bacteria, and other types of cells present therein, as well as for identification of the presence of factors not expected to be present in a sample of urine provided by a healthy person. For such a purpose, the patient typically receives a sterile cup which, the patient is requested to fill with midstream urine. That is, the first pass of the urine is disposed of in, for example, the lavatory, while the midstream urine is collected into the sterile cup. That cup is then capped, marked, and sent to a laboratory for testing. In some cases, a sealed vacuum test tube is inserted to suck a urine sample out of the cup to further ensure that the sample does not get contaminated.

In most medical testing and analysis of urine, the midstream portion of urine is considered the most suitable for this purpose. Therefore, for such analyses and tests, it is necessary to ensure that this midstream urine is not contaminated with the first pass of the urine during the collection procedure. There are solutions designed to collect midstream urine for medical testing that attempt to isolate midstream urine from coming in contact with the first pass urine. Such devices are equipped with mechanisms that divert the flow of urine from a first container of urine to a second container of urine. Then, the sample of urine is taken from the second container, into which the midstream urine was directed to flow.

However, the existing solutions and processes are not always applicable or practical, especially when there is a need for urine samples from infants, patients who are unable to provide a urine sample into a sterile cup, or patients with various disabilities that prevent them from properly functioning so as to provide a desirable sample. Contraptions currently being used are complicated to use and do not have broad applicability. That is, people with disabilities or disorders may find it difficult or impossible to perform the routine required by the urine sampling procedure. As a result, many patients have to provide urine samples by using a catheter, a more costly and risk-prone procedure.

There is further a challenge relating to the fact that the first pass of urine, which is not used due to its contaminations, may mix with the midstream urine coming thereafter. Usually a patient using a cup is requested to first urinate outside of the cup and then into the cup. However, as this is typically done in a private area, it is not clear if the patient actually followed the necessary steps.

It would be, therefore, advantageous to provide a solution for urine sampling that overcomes the deficiencies noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the terms "some embodiments" or "certain embodiments" may be used herein to refer to a single embodiment or multiple embodiments of the disclosure.

Certain embodiments disclosed herein include a urine sampling container comprising a container shell made of a non-porous material, wherein the container shell includes an orifice through which urine enters into the container shell; and a layer of a water-absorbent resin deposited over at least a bottom portion internal to the container shell.

Certain embodiments disclosed herein also includes urine sampling container. The container comprises a container shell made of a non-porous material, the container shell includes an orifice through which urine enters into the container shell; and a first sheath separating an internal portion of the container shell into a first chamber and a second chamber, the sheath being equipped with at least a unidirectional valve preventing flow of urine collected in the first chamber from flowing into the second chamber.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
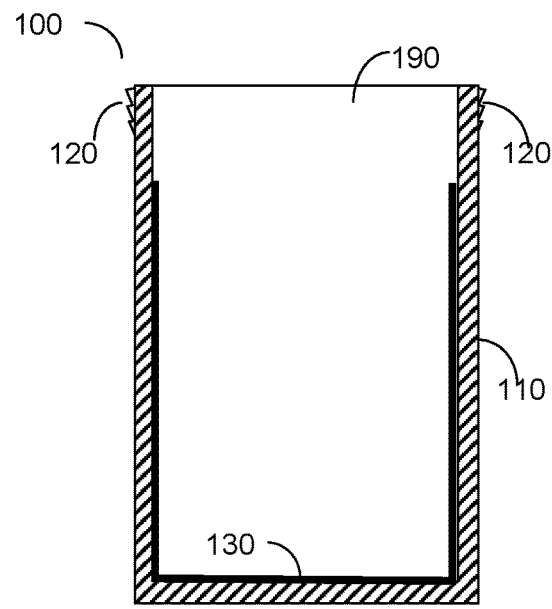
FIG. 1 is a cross-section of a urine sampling container according to one embodiment.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

Some example embodiments provide a container for urine sampling. The container is designed to separate early-stream urine (e.g., a first pass urine) from the midstream, where the midstream is the stream that should be sampled into a sterile container. In bladder-controlled patients, the cooperation of the patient is relied upon, but this is not the case with a large enough population that cannot perform such procedures due to incontinence. According to a first embodiment, a container is coated with compounds that cause the first pass urine to come into contact with an absorbent substance and become inert. Once the compound is consumed, the rest of the midstream urine can be collected for sampling. In a second embodiment, a container is portioned into chambers, where each chamber is connected to the other chamber by means of unidirectional micro-valves. Coating certain chambers with a liquid deterrent substance causes the first pass urine to repel and flow to a chamber from which urine is not sampled, and then causes such chambers to fill once the first chamber is full to capacity.

FIG. 1 depicts an example cross-section of a urine sampling container 100 according to an embodiment. The urine container 100 includes an external shell 110. The upper portion of the external shell 110 may be adapted to accept a cap (not shown), for example, by having screw grooves 120 therein designed to accept screw grooves of the cap. The external shell 110 is made, for example, of a polymer that provides a basically non-porous material, such that the urine contained within the external shell 110 remains therein. The internal portion of the external shell 110 is coated with a water-absorbing resin of types well-known in the art, including, and without limitation, polyacrylate, silica gel, and the like. Typically, a water-absorbent resin, such as polyacrylate, may absorb hundreds of times its own weight in liquid. Accordingly, a quantity of the water-absorbent resin is deposited as a layer 130. In an example embodiment, a few milliliters of urine are gelled by the water absorbent resin.

When a patient provides a urine sample, the first flow of urine is absorbed by the water-absorbing resin and, as a result, becomes inert. This can be achieved by use of proper ratios between the water-absorbent resin in the layer 130 and the amount of first flow urine to be absorbed.

It should be appreciated that a container 100 may have the shape of a cup, a bag, or other shapes, without departing from the scope of the disclosure. In the case where the container 100 is shaped as a bag, the container 100 may have an opening that is adapted to be affixed about the urinary tract, for example, in the case of a human, for the purpose of collecting a urine sample. The affixing to the body may be performed by using biological glue of kinds well-known in the art. Other means of affixing the container to the body may be used without departing from the scope of the disclosure. Once the sampling is complete, the bag may be removed and the sample collected. It should be further appreciated that sampling the urine using a vacuum test tube being pierced by a needle of the cap would be consistent with procedures used currently for urine sampling.

Figure 2:
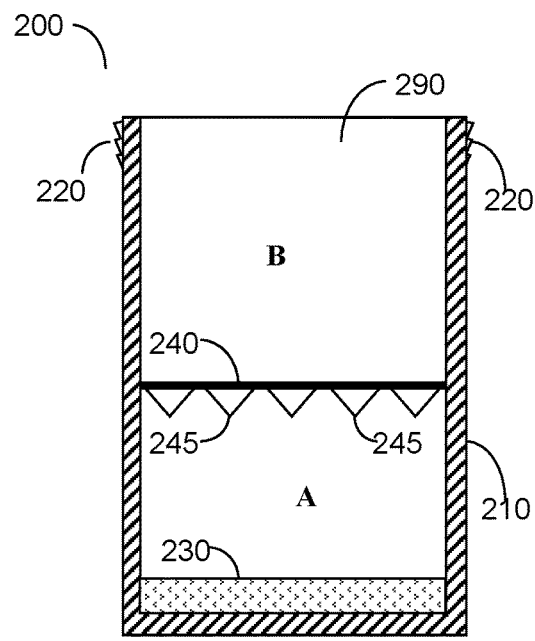
FIG. 2 is a cross-section of a urine sampling container according to one embodiment.

FIG. 2 shows an example cross-section of a urine sampling container 200 according to another embodiment. The urine sampling container 200 includes an external shell 210. The upper portion of the external shell 210 may be adapted to accept a cap (not shown), for example, by having screw grooves 220 therein designed to accept screw grooves of the cap. The external shell 210 is made, for example, but not by way of limitation, of a polymer that provides a basically non-porous material such that the urine contained within the external shell 210 remains therein.

Within the container 200 there is placed a sheath 240 that includes one or more unidirectional valves 245 that are adapted to allow the flow of the urine from chamber "B" of the container 200 to chamber "A" of the container 200, but not vice versa. In one embodiment, an array of micro-unidirectional valves may be used. Chamber "A" is adapted to contain therein an amount of urine that is considered to be the first pass and which is undesirable for the purpose of being used for medical analysis and tests. The midstream urine is contained, therefore, within chamber "B" of the container 200.

In one embodiment, a water-absorbent resin layer 230 is placed within chamber "A." The layer 230 may be made of, without limitation, polyacrylate coatings, and the like. When urine is sampled, the first pass of urine goes through the sheath 240 and, when coming in contact with the water-absorbent resin layer 230, the layer 230 gels and sets therein, thereby separating the first pass of urine from midstream urine. When the chamber "A" is full, the micro-unidirectional valves prevent the urine collected in chamber "A," even if it remains as a liquid, from returning to chamber "B" of the container 200.

In one embodiment, the chamber "B" is at least partially coated by a water-repellent (hydrophobic) coating that repels the urine collected towards the sheath 240 and into chamber "A." Such functionality is provided to repel the first pass of urine and to cause the first pass of urine to flow in the direction of the chambers, thereby reducing the presence of contaminated urine to a minimum.

It should be appreciated that the container 200 may have the shape of a cup, a bag, or other shapes without departing from the scope of the disclosed embodiments. In the case where the container 200 is shaped as a bag, it may have an opening, including at the side of chamber "B," rather than its top, where the opening may be adapted to be affixed about the urinary tract, for example, of a human, for the purpose of collecting a urine sample. The affixing to the body may be performed by using biological glue of kinds well-known in the art. Other means of affixing the container to the body may be used without departing from the scope of the disclosure. Once the sampling is complete, the bag may be removed and the sample is collected. It should be noted that sampling the urine using a vacuum test tube being pierced by a needle of the cap would be consistent with procedures used currently for urine sampling.

Figure 3:
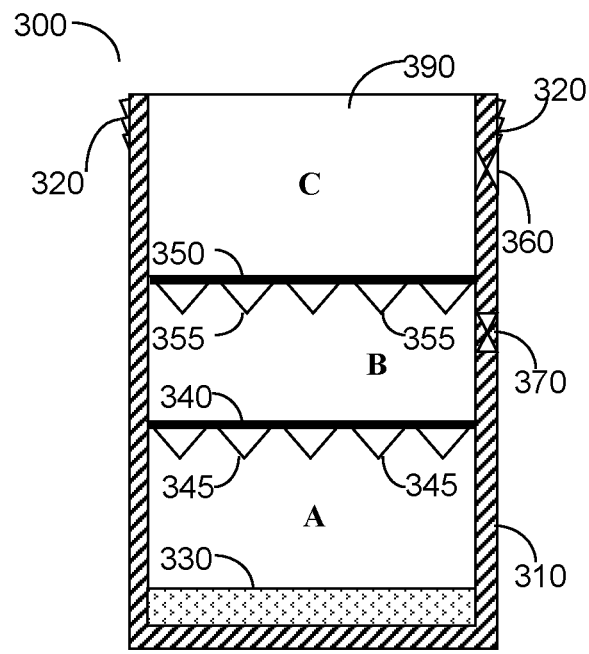
FIG. 3 is a cross-section of a urine sampling container according to yet another embodiment.

FIG. 3 is an example cross-section of a urine sampling container 300 according to a yet another embodiment. The urine sampling container 300 includes an external shell 310. The upper portion of the external shell 310 may be adapted to accept a cap (not shown), for example by having screw grooves 320 therein designed to accept screw grooves of the cap. The external shell 310 is made, for example, of a polymer that provides a basically non-porous material, such that the urine contained within the external shell 310 remains therein.

Within the container 300 there is placed a first sheath 340 which includes one or more unidirectional valves 345 adapted to allow flow of the urine from chamber "B" of the container 300 to chamber "A" of the container 300, but not vice versa. In one embodiment, an array of micro-unidirectional valves may be used. Chamber "A" is adapted to contain therein an amount of urine that is considered to be the first pass and which is undesirable for the purpose of being used for medical analysis and tests. Within the container 300 there is further placed a second sheath 350 that comprises one or more unidirectional valves 355 that are adapted to allow flow of the urine from chamber "C" of the container 300 to chamber "B" of the container 300, but not vice versa.

In one embodiment, an array of micro-unidirectional valves may be used. Chamber "B" is adapted to contain therein an amount of urine that is the midstream urine and, therefore, is usable for medical analysis and tests. The midstream urine is contained therefore within chamber "B" of the container 300.

In one embodiment, a water-absorbent resin layer 330, such as, but not by way of limitation, polyacrylate coatings, or the like, is otherwise placed within chamber "A." When urine is sampled, the first pass of urine goes through the sheath 340 and, when coming in contact with the water-absorbent resin layer 330, it gels and sets therein, thereby separating the first pass of urine from the midstream urine. When the chamber "A" is full, the micro-unidirectional valves prevent the urine collected in chamber "A," even if it remains as a liquid, from returning to chamber "B" of the container 300. In one embodiment, the chambers "B" and "C" are at least partially-coated with a water-repellent (hydrophobic) coating that repels the urine collected toward the respective sheaths, 340 and 350, directing urine into chambers "A" or "B," respectively.

In an embodiment, a unidirectional valve 360 is embodied within chamber "C" to allow overflow of urine within chamber "C" to exit the container. In an embodiment, a sampling valve 370 allows the receipt of, for example, a vacuum test tube for the collection of urine from within chamber "B."

It should be appreciated that the collection of urine using the container described with respect to FIG. 3 is done differently from the embodiment discussed with respect of FIG. 2, as the midstream urine is contained within chamber "B."

It should be further appreciated that the container 300 may have the shape of a cup, a bag, or other shapes, without departing from the scope of the disclosure. In the case where the container 300 is shaped as a bag, it may have an opening, including at the side of chamber "C," rather than its top, which is adapted to be affixed about the urinary tract, for example, of a human, for the purpose of collecting a urine sample. The affixing to the body may be performed by using biological glue of kinds well-known in the art. Other means of affixing the container to the body may be used without departing from the scope of the disclosure. Once the sampling is complete, the bag may be removed and the sample collected. The sampling the urine using a vacuum test tube being pierced by a needle of the cap would be consistent with current procedures used currently for urine sampling. In one embodiment of the container 300, the pressure required to open or close the valves 355 is greater than the pressure required to open or close the valves 345.

The containers 100, 200, and 300 described in FIGS. 1 through 3, have openings, also referred to as orifices, 190, 290, or 390, respectively, through which the urine flows into the container. As noted above, these may also be at the side of the container 100, 200, or 300, respectively. When the container (100, 200, or 300) is to be affixed to the body of a patient, it may cause discomfort and, therefore, a flexible silicon mesh (not shown) may be affixed to the opening (190, 290, or 390 as the case may be). The flexible silicon mesh prevents direct contact of the urinary tract with the inner portion of the container (100, 200, or 300). In any of the embodiments where biological glue is used, the biological glue may coat an area about the orifice (190, 290, or 390), enabling the affixing of the container (100, 200, or 300) to a patient at the urinary tract. Other means of affixing the container to the body may be used without departing from the scope of the disclosure.

It should be appreciated that the orifice of any of containers 100, 200, or 300 may be positioned at the top of the container or at a side of the container 100, 200, or 300 at a position closest to the top of the container. Such configurations provide for the urine to flow through the chambers, in particular "B" and/or "C," in the desired sequence. In yet another embodiment, the water-absorbent resin may be mixed with a neutralizing compound, such as, but without limitation, a disinfectant, to neutralize the effects of the first pass of urine.

Figure 4:
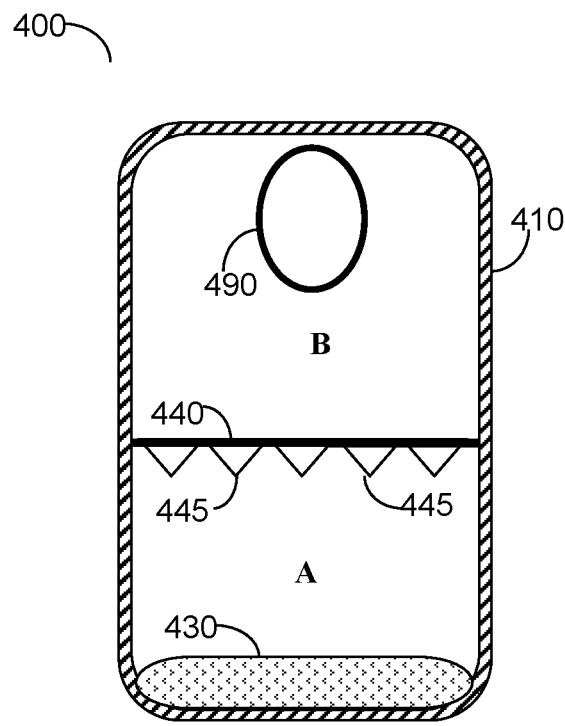
FIG. 4 is a cross-section of a urine sampling container according to yet another embodiment.

FIG. 4 is an example cross-section of a urine sampling container 400 according to a fourth embodiment. In this embodiment, a bag embodiment similar to the urine sampling container 200 is shown. Accordingly, the orifice 290 of FIG. 2, is an orifice 490 located on the side of the container 400 within the area of chamber "B" of the container 400.

A sheath 440, including one or more valves 445 allowing the flow of urine from chamber "B" to chamber "A," but not vice-versa, is also shown. In one embodiment, a water-absorbent resin layer 430 is provided within chamber "A." In one embodiment, an array of micro-unidirectional valves may be used. The water-absorbent resin layer 430 is designed to absorb the urine into an inert gel, thereby ensuring the urine does not impact the midstream urine, which is captured within chamber "B." FIG. 4 is provided merely for pedagogical reasons to demonstrate the possibility of implementing the teachings herein in a bag for urine collection according to the principles disclosed herein and applicable also with regards to FIGS. 1 and 3.

It should be appreciated that the orifice 490 may be gender adapted, i.e., a female would have an orifice 490 adapted to fit the urinal tract of a female patient, while a male would have an orifice 490 adapted to fit the urinal tract of a male patient. Furthermore, embodiments that accommodate for the difference in size and shape depending on, for example, age, are also possible without deviating from the scope of the disclosure.

Figure 5:
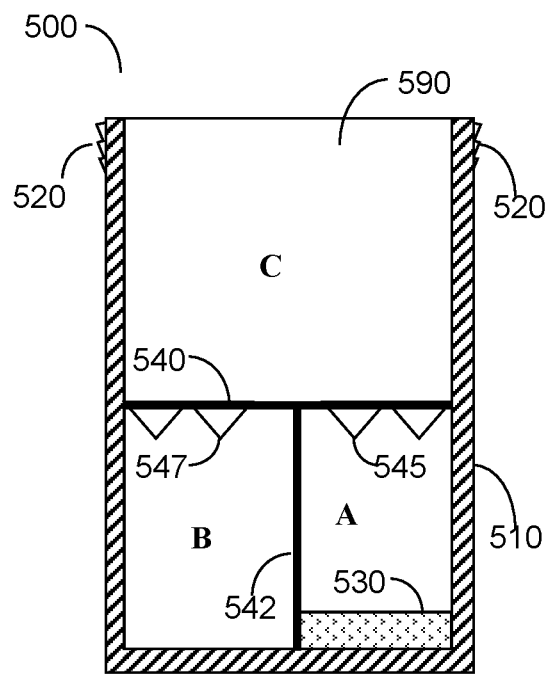
FIG. 5 is a cross-section of a urine sampling container according to yet another embodiment.

FIG. 5 depicts an example cross-section of a urine sampling container 500 according to a fifth embodiment. The urine sampling container 500 includes an external shell 510. Urine enters the urine sampling container through orifice 590 and passes into chamber "C," where the chamber "C" located before side-by-side chambers "A" and "B." In one embodiment, the walls and floor of chamber "C" are coated with a layer of hydrophobic material that repels the urine from remaining in the "C" chamber if an exit is possible. Initially, the urine may flow into chamber "C," which is separated from chambers "A" and "B" by a sheath 540. A barrier sheath 542 separates chambers "A" and "B".

A portion of sheath a 540 of chamber "A" is equipped with unidirectional valves 545 that open under a predetermined minimal pressure, thereby collecting therein the first pass of urine. The number of valves may be equal to or greater than one. Once the container is filled and under internal pressure of the urine collected therein, the valves 545 may close. In one embodiment, the unidirectional valves 545 are an array of unidirectional micro-valves. Further, in one embodiment, a water-absorbent resin 530 is deposited in chamber "A," such that when the urine enters chamber "A," it solidifies or gels therein. Once the chamber "A" is filled, urine continues to collect in chamber "C" until enough pressure is built to cause the one or more unidirectional valves 547 to open.

The pressure for opening the valves 547 is greater than the pressure necessary to open the unidirectional valve 545 protruding from the sheath 540 into chamber "B," ensuring that urine first flows into chamber "A" and, only then, into chamber "B." One of ordinary skill in the art would readily appreciate that an external side of chamber "B" may be equipped with a sampling valve (not shown) to allow the extraction of urine for analysis purposes. Furthermore, chamber "C" may be equipped with a relief valve to allow overflow urine to exit chamber "C." The screw grooves 520 have been described before and, therefore, their function is not repeated herein.

Figure 6:
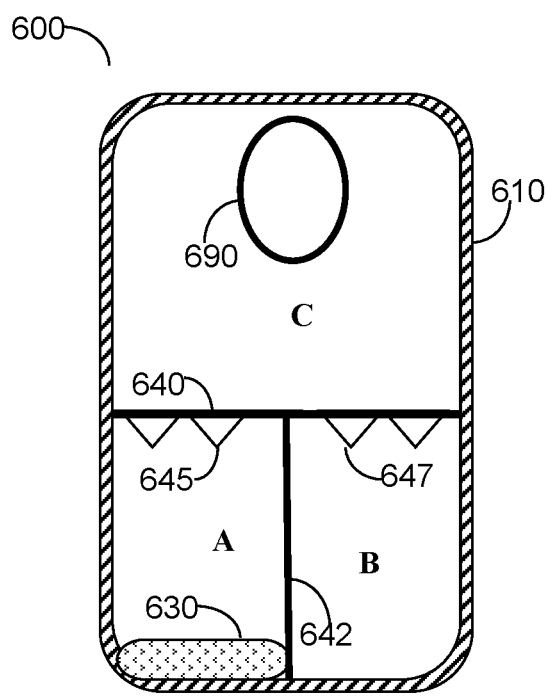
FIG. 6 is a cross-section of a urine sampling container according to yet another embodiment.

FIG. 6 depicts an example cross-section of a urine sampling container 600 according to another embodiment. The urine sampling container 600 includes an external shell 610. Other than being a bag-like container, the container 600 operates similarly to the container 500 described with respect of FIG. 5. Therefore, the function of the chambers "A," "B," and "C" in FIG. 6 are similar to those described in FIG. 5.

The unidirectional valves 645 function similarly to the unidirectional valves 545. The unidirectional valves 647 function similarly to the one or more unidirectional valves 547. The sheath 640 functions similarly as the sheath 540, and the barrier sheath 642 functions similarly to the barrier sheath 542. The orifice 690 through which urine flows into chamber "C" protrudes from a side of the container 600 within the confinement of chamber "C." In an embodiment, chamber "A" may contain a layer of water-absorbing resin for purposes described herein in greater detail. In another embodiment, at least a portion of chamber "C" is coated with a hydrophobic layer as described in greater detail herein.

It should be appreciated that in any of the embodiments described herein, an initial unidirectional valve (not shown) may be fitted to prevent any direct contact between the body of a patient and the collected urine. Furthermore, any embodiment may be fitted into a diaper.

Certain embodiments may further include a warning device (not shown) that provides an indication that a sufficient amount of urine has been collected in the chamber where the midstream urine is stored. The warning device may be, as examples and without limitation, a Bluetooth low energy device, a radio-frequency identification device (RFID) tag, or the like, as well as any combination thereof.

It should be noted that the hydrophobic materials discussed herein may include, without limitation, materials such as silica or titania particles using a technique such as sol-gel. It should be further noted that certain elements of one container may be used in another container configuration without departing from the scope of the disclosure.

All examples and conditional language recited herein are intended for pedagogical purposes to aid the reader in understanding the principles of the disclosed embodiments and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A urine sampling container, comprising:
   a container shell made of a non-porous material, the container shell includes an orifice through which urine enters into the container shell;
   a first sheath separating an internal portion of the container shell into a first chamber and a second chamber;
   at least a first unidirectional valve arranged on the first sheath to prevent flow from the second chamber to the first chamber, wherein the at least a first unidirectional valve allows urine to flow from the first chamber to the second chamber, whereby a urine sample, apart from a first pass of urine collected in the second chamber, is collected in the first chamber;
   a second sheath separating the second chamber into a first compartment and a second compartment, wherein each of the first compartment and the second compartment has at least one of the at least a unidirectional valve of the first sheath; and
   wherein at least one of the at least a unidirectional valve of the first compartment has a first predetermined opening pressure, wherein the at least one of the at least a unidirectional valve of the second compartment has a second predetermined opening pressure, and wherein the first predetermined opening pressure is less than the second predetermined opening pressure.

2. The urine sampling container of claim 1, further comprising:
   a layer of water-absorbent resin deposited on at least a portion of the second chamber.

3. The urine sampling container of claim 1, wherein the first compartment further comprises;
   a layer of water-absorbent resin deposited on at least a portion of the second chamber.

4. The urine sampling container of claim 1, wherein the first chamber is at least partially coated by a water-repellent substance.

5. The urine sampling container of claim 4, wherein the water-repellent substance is hydrophobic.

6. The urine sampling container of claim 1, wherein the second compartment is adapted to receive a vacuum test tube for collection of a midstream urine collected therein.

7. The urine sampling container of claim 1, wherein the at least a first unidirectional valve prevents the first pass urine from flowing back into the first chamber upon the second chamber reaching full to a capacity.

\* \* \* \* \*